United States Patent [19]

Hurtig et al.

[11] 4,091,654
[45] May 30, 1978

[54] MAGNETIC RECORDING MEMBER ABRASION TESTER

[75] Inventors: Roy E. Hurtig, Saratoga; Stanley I. Rojo, San Jose, both of Calif.

[73] Assignee: Memorex Corporation, Santa Clara, Calif.

[21] Appl. No.: 788,462

[22] Filed: Apr. 18, 1977

[51] Int. Cl.² .............................................. G01N 3/56
[52] U.S. Cl. ..................................................... 73/7
[58] Field of Search ................ 73/7, 432 SD; 356/210

[56] References Cited

U.S. PATENT DOCUMENTS

| | | | |
|---|---|---|---|
| 3,359,783 | 12/1967 | Scheiman et al. | 73/7 |
| 3,554,007 | 1/1971 | Hu | 73/7 |
| 3,612,891 | 10/1971 | Ward et al. | 73/7 X |
| 3,753,093 | 8/1973 | Gardner et al. | 73/7 X |
| 3,834,219 | 9/1974 | Brauer | 73/7 |
| 3,961,521 | 6/1976 | Bailey et al. | 73/7 |

Primary Examiner—S. Clement Swisher

[57] ABSTRACT

A device and method are disclosed for testing the abrasion quality of a magnetic recording member to cause recording head wear. A magnetic recording member to be tested is moved past a dummy recording head, the smoothness of which has been determined before the head is contacted with the magnetic recording surface. After a predetermined contact between the dummy head and the tape, the smoothness of the head is again determined which is a direct function of the abrasion characteristics of the tape. The smoothness of the dummy head is determined by means of a non-contact photonic sensor which converts reflective light from the surface of the head into a specific voltage output.

18 Claims, 6 Drawing Figures

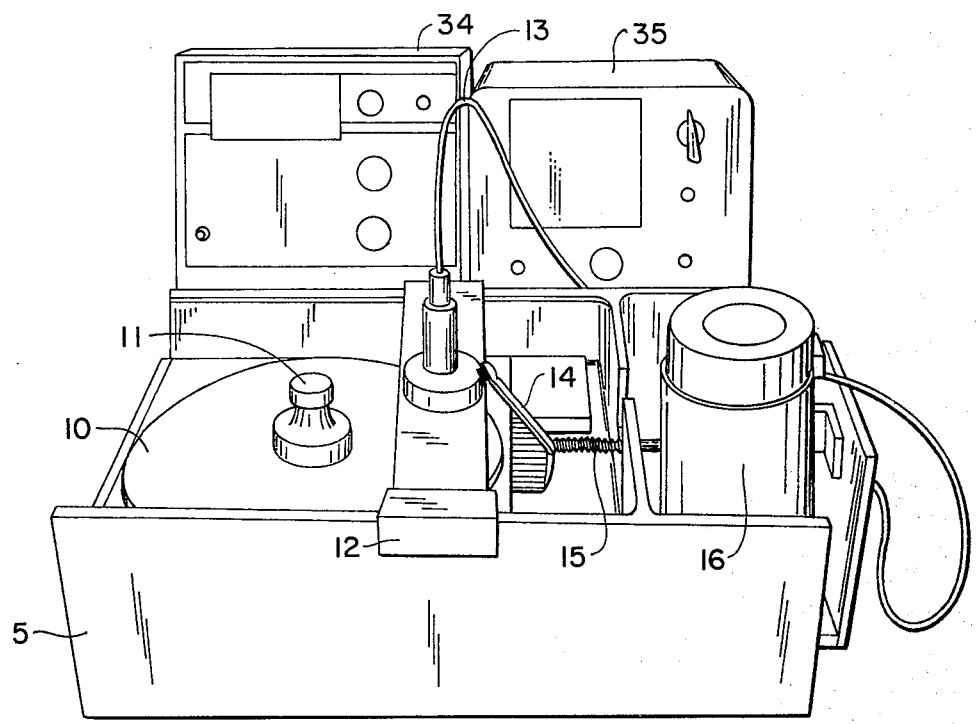
FIG._1.
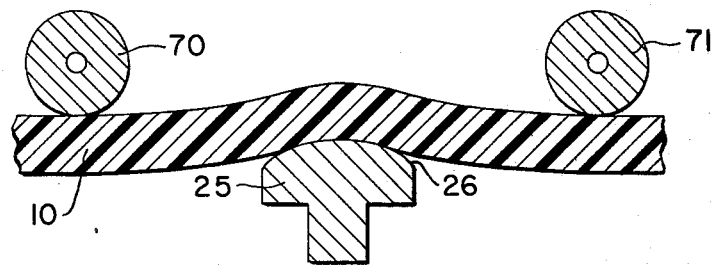
FIG._2.
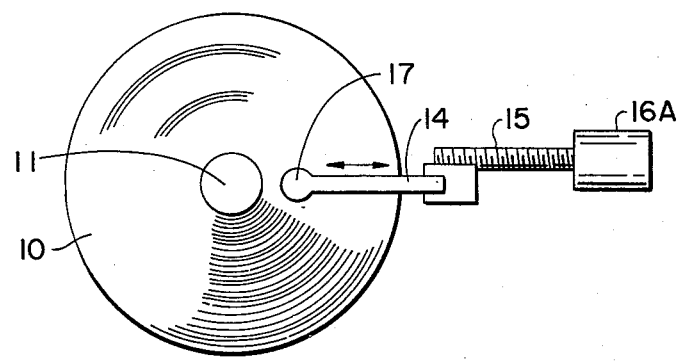
FIG._3.

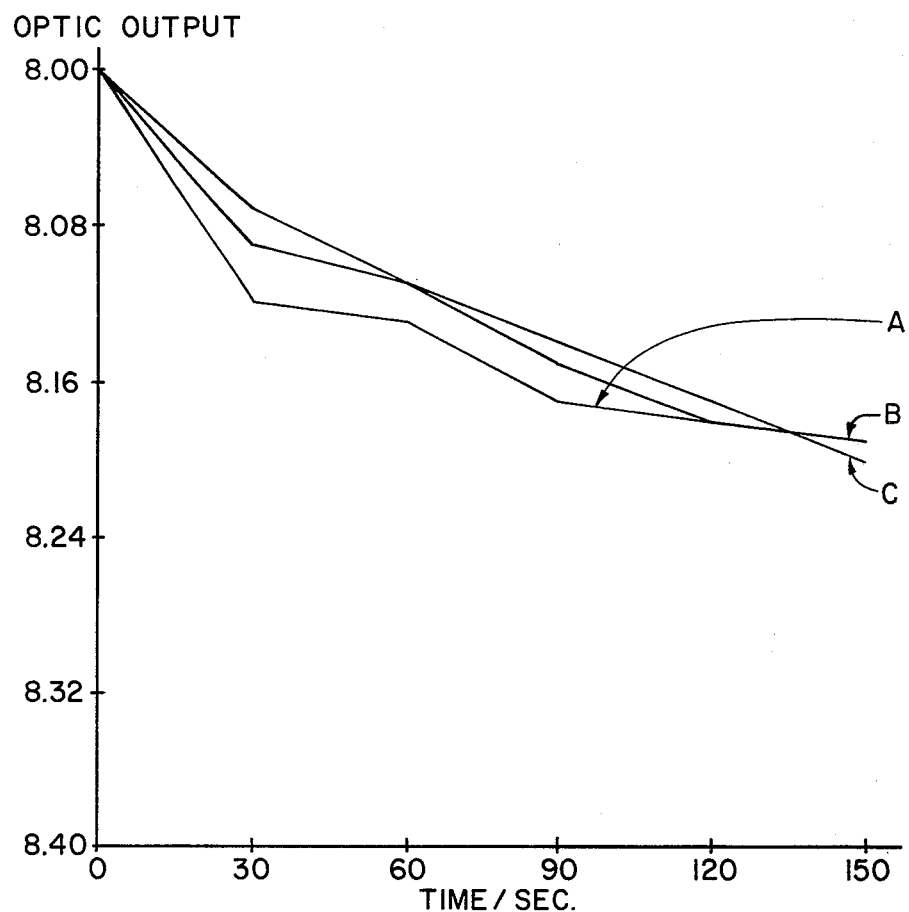
FIG._4.
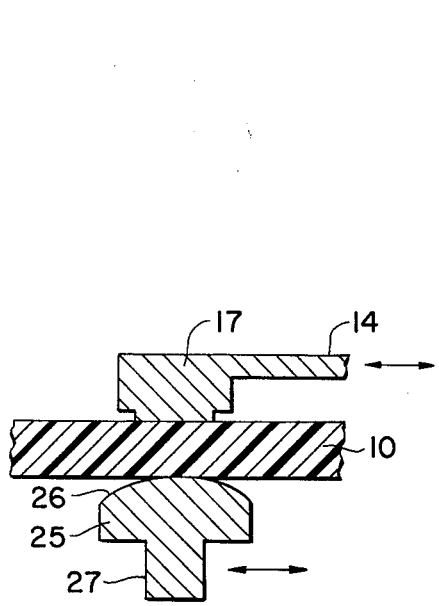
FIG._5A.
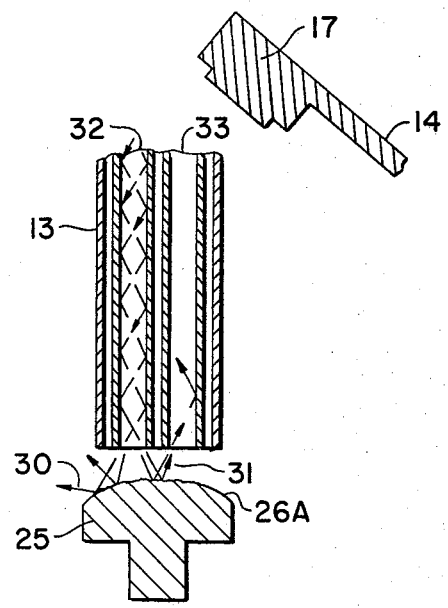
FIG._5B.

MAGNETIC RECORDING MEMBER ABRASION TESTER

BACKGROUND OF THE INVENTION

Magnetic recording members are traditionally made by spraying or coating onto an appropriately shaped substrate, a fluid mixture of magnetic particles and resinous binder and thereafter curing the resinous binder to adhere the magnetic particles to each other and to the substrate. Examples of such fluid mixtures can be found in U.S. Pat. No. 2,914,480 to Hagopian and U.S. Pat. No. 3,058,844 to Johnston et al. Conventional magnetic recording members contain additional constituents for various purposes. For example, U.S. Pat. No. 3,622,386 to Larsen teaches the addition of an abrasive particle to a magnetic recording element in order to improve the usable life of the element and decrease the hazards of permanent damage to the recording surface and the recording head as a result of an occasional head crash.

Magnetic coating compositions have been made with a wide variety of binder systems both thermoplastic and thermosetting, and many of these magnetic coatings have very desirable properties for particular applications. However, substantially all of the magnetic coatings have disadvantages from the standpoint of their magnetic properties, their physical ability to withstand abrasion, their abrasive effect upon recording heads and their processing characteristics.

Before a tape product can be marketed commercially, it is desirable to perform several tests to determine not only its memory characteristics but also physical characteristics such as abrasive quality. At the present time, there is no existing method which satisfactorily correlates tape abrasion to head wear. Prior to the present invention, a rough correlation could be established by running a tape product through commercial apparatus for an extended period of time, e.g., 24 hours, and then microscopically examining the magnetic head and tape surface for wear. Other abrasive means have been attempted, even using dummy head blocks in which the amount of head material which has been worn from the block was measured, but due to the difficulty in fabricating uniform blocks, such tests have proven to be inaccurate. Existing methods are useful as guides but are time consuming and expensive to run and therefore of little interest as a production or quality control tool on a continuous basis. Furthermore, such a protracted tests results in both magnetic tape wear and magnetic head wear. The magnetic head follows a constant path on the magnetic tape and actually cuts a groove within said tape such that after a protracted period during the test, one is no longer "testing" the commercial tape product but is instead merely running the magnetic head over a smoothed or polished tape surface.

SUMMARY OF THE INVENTION

According to the present inventon, all of the above-noted problems are eliminated. More particularly, a method of testing the abrasive quality of a magnetic recording member is presented in which the test can be carried out in a matter of minutes without any appreciable damage to the recording member's surface itself while the magnetic head can be "tested" for abrasion without ever touching or otherwise interfering with the head surface. Furthermore, the method of the present invention is readily reproducible an various recording members can be qualitatively compared for their respective abrasive qualities. Briefly stated, the invention includes means for moving a flexible disc or other magnetic recording surface past a head element and means which maintains a uniform predetermined pressure between said head element and the magnetic recording surface. During contact between the magnetic head and magnetic recording surface, the magnetic head together with the pressure means are in constant radial motion so that the magnetic head does not contact a single channel of the tape or disc surface during the test.

In performance of the present invention, an actual magnetic recording head is replaced with an element hereinafter denominated as a "dummy" head. This dummy head comprises a metal button, such as stainless steel, which can have a curved surface which is designed to contact the magnetic recording surface. The button is highly polished and quite reflective, the degree of polishing being a design parameter which will be discussed at a later point in this application.

Before conducting the test, a photonic sensor such as that available from MTI Instruments and known as the KD-100 FOTONIC SENSOR is employed. More specifically, a photo emitter-detector comprising a fiber optic emitter-collector is held at a constant distance from the head surface. The fiber bundle emits a specific predetermined quantity of light which is directed toward the head surface and is reflected therefrom back to the collector fiber bundle of the device. The amount of light which is reflected and thus collected by the fiber bundle collector is directly related to the smoothness of the head surface. The collected light is converted into a voltage output which is read on, for example, the MTI FOTONIC SENSOR. As the dummy head traverses a magnetic member's surface, grooves are cut into the head which are a direct function of the abrasive quality of the recording member. A grooved surface on a flat head reflects or scatters the light away from the fiber optic collector, but a curved head increases or gathers the light into the fiber optic collector increasing the sensor output when the surface becomes increasingly grooved. By beginning with a polished head of known smoothness and measuring the reflective qualities of the dummy head after predetermined and controlled contact, one can easily determine the relative abrasive qualities of any number of magnetic recording member products.

The invention, both as to its construction and method of operation, together with further features and advantages thereof, may best be understood by reference to the following description taken in connection with the accompanying illustrative drawings in which:

FIG. 1 is a perspective view of one embodiment of the present invention adapted to test flexible disc magnetic recording surfaces;

FIG. 2 is an enlarged cross sectional view showing contact between the dummy head and magnetic recording element;

FIG. 3 is a partial sectional view of the mechanism for advancing and withdrawing the dummy head assembly;

FIG. 4 is a graph of tests run on various tape products;

FIG. 5A is a further enlarged cross sectional view showing contact between the dummy head and magnetic recording elements; and FIG. 5B is an enlarged cross sectional view showing the fiber optic emitter-collector being used to test the surface of the dummy head element.

Referring to the drawings and in particular to FIG. 1, a device is disclosed for measuring the abrasive properties of a flexible disc member 10. The flexible disc member is maintained on a turntable (not shown) within housing 5, the speed of said turntable being controlled by controller 35. The device of FIG. 1 is shown before any testing is done wherein counterweight arm 14 is in a raised position so that fiber optic bundle 13 is exposed directly to dummy head 25 (FIG. 5B) in order to measure the smoothness of the head surface. Dummy heads are selected to be of the general shape as shown in FIG. 5A with a curved upper surface 26 and base portion 27. Such a configuration is chosen in order to approximate the physical contact which occurs between a magnetic recording surface and a magnetic head in actual recording applications. Heads are usually selected to be of a relatively hard material, such as stainless steel, although other metallic materials could be chosen. The heads are polished to a standard uniform smoothness such as approximately 2 microinches; although this is not critical as long as the dummy head surface is smoother than the surface of the magnetic recording element.

During actual operation, a new, highly polished dummy head 25 is placed within housing 5 directly below the end of counterweight arm 14 at 17. The head-counterweight combination are attached to a worm gear 15 and driven by a motor 16/16A which causes the head-counterweight combination to radially traverse magnetic recording element 10 from its periphery to a point proximate to center hub 11. Although worm gear 15 and driving motor 16 could be eliminated such that dummy head 25 contacts a single path on magnetic recording element 10, it is preferable to cause dummy head 25 and counterweight 17 to traverse the magnetic coating radially such that the magnetic recording layer acts upon the dummy head while the dummy head does not wear a track within the recording element.

Before magnetic recording element 10 is placed upon the turntable, the smoothness of a new dummy head is determined by means of fiber optic emitter-collector 13 and photonic sensor 34. The voltage output reading of the sensor can be calibrated to a specific starting point, i.e., a "zero" reading so that various magnetic recording elements can be compared by using different dummy heads polished to approximately the same but not identical smoothness.

A magnetic recording element 10 is then placed upon the turntable and central spindle 11 is used to secure the recording element thereto. Arm 14 and counterweight 17 are caused to lay down onto the recording element and assume a position shown in detail in FIG. 5A wherein counterweight 17 is caused to press the recording member against the top of the dummy magnetic head at surface 26. The turntable can be caused to rotate at virtually any desired speed. In order to duplicate commercial operation, it is preferable to choose a speed of approximately 360 rpm. Motor 16 is then actuated causing dummy head and counterweight assembly to move radially as shown in FIG. 3.

Referring now to FIG. 5B, a dummy magnetic head 25 is shown after a number of passes in contact with a magnetic recording medium. Top surface 26A of dummy magnetic head 25 is scored or roughened as a function of the abrasive property of the recording member surface. After a test run is complete, counterweight arm 14 is withdrawn (as shown in FIG. 1) and fiber optic emitter-collector is brought proximate to the dummy head surface. The gap between the fiber optic bundle and the dummy head surface is not critical although it is found that a gap of approximately 10-35 mils provides optimum output voltage on the photonic sensor. However, once the gap has been selected, it should be kept at a constant value in that the gap size directly relates to the voltage reading on the photonic sensor. Light travels within each fiber optic bundle and exits the emitter in a 60° cone as shown by light beams 30 emanating and bouncing off of the dummy head surface. Within the entire bundle 13, next to emitter 32, is collector 33. A certain fraction of light beams 30 are collected as shown schematically by light beams 31. As stated previously, this process was carried out with dummy head 25 before being contacted with magnetic recording surface 10. Thus, a specific voltage reading representing the fraction of light 31 bouncing from surface 26 and being collected by collector 33 was noted. Any change in collected light is shown by a corresponding change in voltage on the photonic sensor. As dummy head 25 becomes increasingly worn, more light is reflected into collector 33 due to grooves channeled into curved surface 26A. As previously stated, if surface 26A were flat, there would be a voltage decrease as the surface became more grooved.

The results which are achieved can be plotted as shown in FIG. 4. This graph was generated by viewing dummy magnetic recording heads at 30, 60, 90, 120 and 150 second intervals and recording the voltage output generated from the photonic sensor at these relative periods of time. As can be seen, the sensor was calibrated such that each new magnetic recording head gave an initial output voltage of 8 volts. As would be expected, the initial 30 second measurement resulted in the greatest increase in optic output while the optic output and corresponding abrasion of the dummy magnetic head seem to level off after 150 seconds of contact. A quick examination of FIG. 4 indicates to one of ordinary skill in the art the comparative abrasive properties of various magnetic recording members A, B and C.

Referring to FIG. 2, a further variation of the present invention is disclosed. Although it has been stated that the present invention is adaptable to testing the abrasive qualities of virtually any magnetic recording surface, up to now the invention has been described in terms of the testing of flexible discs. Flexible disc testing requires a turntable to spin the disc and a counterweight to press the magnetic recording medium against the dummy head. FIG. 2 shows the cross section of the magnetic recording medium-dummy head interface wherein computer tape is the medium being tested.

In the mode of FIG. 2, a standard size computer tape reel is caused to pass once over dummy head 25. Computer tape 10 passes under metallic cylinders 70, 71 which cause tape 10 to contact surface 26 at a certain constant pressure. Thus, counterweight 17 can be eliminated in this mode. Also, because the tape makes only one pass over the dummy head, there is no need to radially move the head arm assembly, so that motor 16 and its attendant gearing, etc. can also be eliminated. Once the reel of magnetic tape has run through the tester in contact with the dummy head, the smoothness of the head is measured just as described above.

The present invention offers a reliable, fast, efficient and reproducible test for the abrasive properties of a magnetic recording member. It should further be noted that at no time during the abrasion testing operation is the dummy head ever contacted by the technician performing the test. All measurements are non-contact which provides for ease of operation and reproducibility of results.

Although the device of the present invention was shown as being adapted to test flexible discs on a turntable and computer tape, the instant device could be used for testing virtually any magnetic recording surface while remaining within the spirit and scope of the present invention. One of ordinary skill in the art could easily conceive of substitute magnetic recording material drive means when desiring to test other configurations of magnetic recording medium.

What is claimed is:

1. A method of determining the abrasion capability of a magnetic recording member to cause recording head wear comprising:
   A. determining the smoothness of a magnetic head surface by means of a fiber optic emitter-collector;
   B. contacting the surface of said magnetic head to a moving magnetic recording member at a predetermined constant pressure;
   C. maintaining said contact for a predetermined period of time;
   D. removing the magnetic head from the moving magnetic recording member; and
   E. determining the relative smoothness of the magnetic head surface by means of a fiber optic emitter-collector.

2. The method of claim 1 wherein the magnetic head is a highly polished dummy head.

3. The method of claim 2 wherein the magnetic head has a curved surface.

4. The method of claim 2 wherein the magnetic head is composed of stainless steel.

5. The method of claim 1 wherein the magnetic head is in constant movement while in contact with the magnetic recording member such that said magnetic head is caused to contact substantially the entire width of the magnetic recording member.

6. The method of claim 1 wherein the magnetic head is caused to contact the surface of the magnetic tape at a pressure from 0.2 to 1.0 grams.

7. The method of claim 1 wherein the magnetic recording member comprises a flexible magnetic disc rotated upon a turntable at a constant speed.

8. The method of claim 7 wherein said turntable is caused to rotate at approximately 360 revolutions per minute.

9. The method of claim 1 wherein said magnetic recording member is computer tape.

10. A device for determining the abrasion capability of a magnetic recording member to cause recording head wear comprising:
    A. a magnetic recording member;
    B. a magnetic head;
    C. means for moving said magnetic recording member at a constant predtermined speed past said magnetic head;
    D. means for causing said magnetic head to contact said magnetic recording member at a constant predetermined pressure while the magnetic recording member is caused to move relative to the magnetic head; and
    E. means for measuring the smoothness of the magnetic head both before and after the magnetic head has contacted the magnetic recording member surface by means of fiber optic emitter-collector.

11. The device of claim 10 wherein said magnetic recording member is computer tape.

12. The device of claim 10 further comprising means for moving the magnetic head relative to the magnetic recording member surface.

13. The device of claim 10 wherein the magnetic recording member comprises a flexible magnetic disc rotated upon a turntable at a constant predetermined speed.

14. The device of claim 13 wherein said turntable is caused to rotate at approximately 360 revolutions per minute.

15. The device of claim 10 wherein the magnetic head is caused to contact the surface of the magnetic recording member at a pressure from 0.2 to 1.0 grams.

16. The device of claim 10 wherein said magnetic head is a highly polished dummy head.

17. The device of claim 16 wherein said magnetic head has a curved surface.

18. The device of claim 16 wherein said magnetic head is composed of stainless steel.

* * * * *